United States Patent
Llewellyn-Hyde et al.

(10) Patent No.: US 8,814,828 B2
(45) Date of Patent: *Aug. 26, 2014

(54) AUTOINJECTOR WITH DESHIELDER COMPRISING TAMPER EVIDENCE MEANS

(75) Inventors: David Llewellyn-Hyde, Basingstoke (GB); Vernon Rich, Swindon (GB); Hervé Abry, Champagnier (FR); Frédéric Perot, Saint Paul de Varces (FR); Jérôme Blanc, Saint Martin le Vinoux (FR); Lionel Maritan, Pierre Chatel (FR)

(73) Assignee: Becton Dickinson France, Le Point de Claix (FR)

( * ) Notice: Subject to any disclaimer, the term of this patent is extended or adjusted under 35 U.S.C. 154(b) by 903 days.

This patent is subject to a terminal disclaimer.

(21) Appl. No.: 12/679,928

(22) PCT Filed: Sep. 25, 2007

(86) PCT No.: PCT/IB2007/003974
§ 371 (c)(1),
(2), (4) Date: Jun. 28, 2010

(87) PCT Pub. No.: WO2009/040603
PCT Pub. Date: Apr. 2, 2009

(65) Prior Publication Data
US 2010/0268169 A1 Oct. 21, 2010

(51) Int. Cl.
*A61M 5/20* (2006.01)
*A61M 5/00* (2006.01)

(52) U.S. Cl.
USPC ........................................ 604/135

(58) Field of Classification Search
USPC .................. 604/135, 263, 131, 111
See application file for complete search history.

(56) References Cited

U.S. PATENT DOCUMENTS

| | | | |
|---|---|---|---|
| 4,667,837 A | 5/1987 | Vitello et al. | |
| 5,137,516 A | 8/1992 | Rand et al. | |
| 5,295,965 A | 3/1994 | Wilmot | |
| 5,506,015 A | 4/1996 | Frederiksen et al. | |
| 6,193,688 B1 | 2/2001 | Balestracci et al. | |
| 6,585,702 B1 | 7/2003 | Brunel | |
| 8,313,470 B2 * | 11/2012 | Abry | 604/198 |

FOREIGN PATENT DOCUMENTS

| | | |
|---|---|---|
| GB | 2 424 836 A | 4/2005 |
| WO | 2006/052737 A1 | 5/2006 |
| WO | 2007/036676 A1 | 4/2007 |

* cited by examiner

*Primary Examiner* — Nicholas Lucchesi
*Assistant Examiner* — Pritesh Patel
(74) *Attorney, Agent, or Firm* — Hoffmann & Baron, LLP

(57) ABSTRACT

The invention relates to a device (1) for automatic injection of a product into an injection site, said device (1) further comprising a needle (6) and a needle shield (2) for protection of said needle (6) prior to use of said device, and a housing (300) receiving the container (50) and a deshielder (8) for removing said needle shield (2) from said device (1), said deshielder (8) being coupled to said needle shield (2) and being mounted on the housing (300) in a separable manner, for example through breakable or snap-fit means, said deshielder (8) comprising tamper evidence means that are activated by the removal of at least one part of said deshielder (8). Said at least one part of said deshielder (8) can be removed from the housing (300) by exerting a traction force equal or less to 30 N.

27 Claims, 11 Drawing Sheets

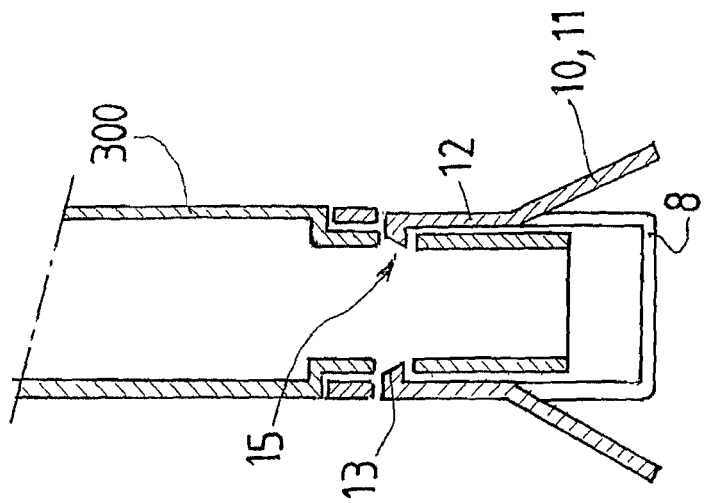
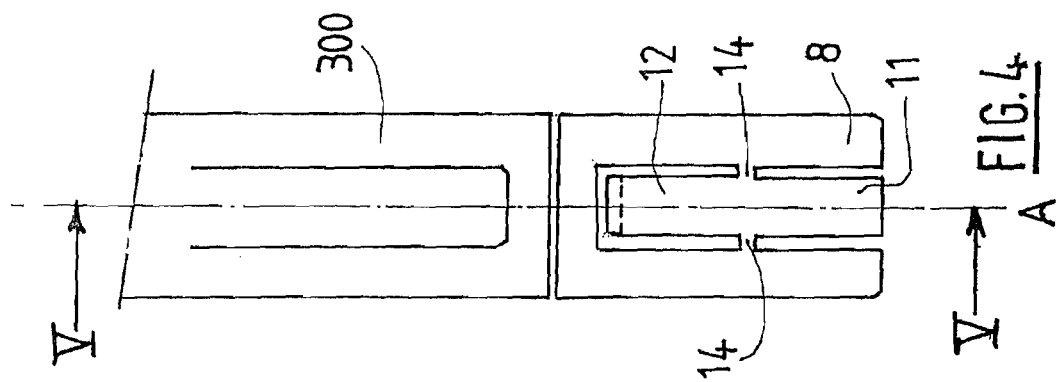
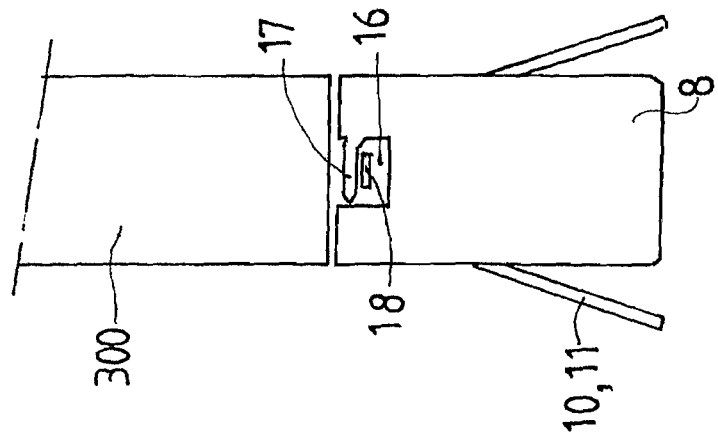

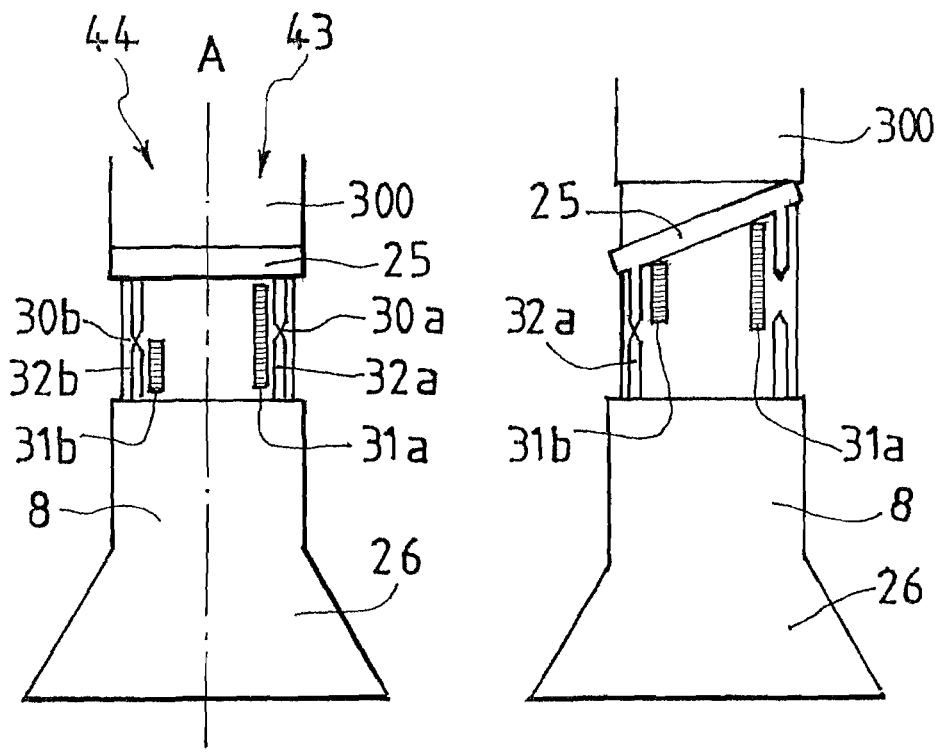
FIG.23
FIG.24
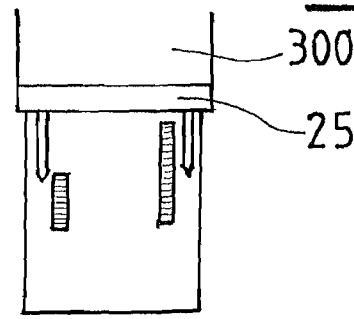
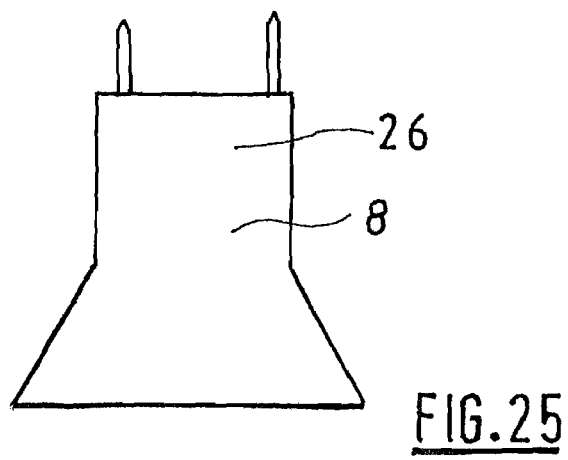
FIG.25

AUTOINJECTOR WITH DESHIELDER COMPRISING TAMPER EVIDENCE MEANS

The invention relates to a device for automatic injection of a product into an injection site.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

In the injection devices of the prior art, the product to be injected is generally carried by a container having an open proximal end and a substantially closed distal end and having a reservoir defined therebetween, and a needle provided at the distal end and in fluid communication with the reservoir to provide an outlet port for the product from the container, and a piston provided in the container and movable with respect with the container, the movement of the piston causing the product to be expelled from the container through the needle, said device further comprising a needle shield for protection of said needle prior to use of said device, and a housing receiving the container and a deshielder for removing said needle shield from said device, said deshielder being coupled to said needle shield and being mounted on the housing in a separable manner, for example through breakable or snap-fit means, said deshielder comprising tamper evidence means that are activated by the removal of at least one part of said deshielder.

The removal of said part of the deshielder is generally difficult for ill people with declined movement and force, because of the high force needed to separate said part of the deshielder from the housing.

Therefore, there is a need to facilitate the use of such device.

In addition, the holding of said part of the deshielder on the housing needs to be sufficient to avoid any accidental removal of said part, for example during manufacture or handling of the device.

The invention meets these needs by proposing a device for automatic injection of a product into an injection site, said device comprising:
- a housing capable of receiving a container;
- a needle shield for protection of a needle provided on the container prior to use of said device; and
- a deshielder for removing said needle shield from said device, said deshielder being coupled to said needle shield and being mounted on the housing in a separable manner, for example through breakable or snap-fit means, said deshielder comprising tamper evidence means that are activated by the removal of at least one part of said deshielder, characterized in that said at least one part of said deshielder can be removed from the housing by exerting a force equal or below 30 N.

Preferably, said force ranges from 2 to 30 N.

According to an embodiment of the invention, said tamper evidence means comprise at least one peg located on the housing, at least one window located on the deshielder and at least one frangible tongue extending into the window, in a direction substantially perpendicular to the longitudinal axis of said device, said peg being engaged into the window before activation of the tamper evidence means, said peg being designed to break said frangible tongue when said part of the deshielder is removed from the housing.

Preferably, said window extends from the proximal end of the deshielder.

According to a an additional feature of the invention, the deshielder comprises at least one leg articulated on the deshielder and extending along the longitudinal axis of said deshielder, said leg comprising an end forming a hook that cooperate with at least one complementary recess formed in the housing, so as to couple said deshielder to said housing.

Alternatively, the deshielder comprises a tubular part receiving a part of the housing, said window being formed on said tubular part, said deshielder comprising at least two legs extending into the window, in the proximal direction, the free ends of the legs being linked by a frangible tongue.

Preferably, in the removed state of the deshielder, the frangible tongue is separated from at least one of the legs, the free ends of said legs then defining a stop on which the peg comes in abutment, thereby preventing the deshielder to be put back on the housing.

According to another embodiment of the invention, said at least one frangible tongue comprises a first and second tabs, each tab comprising a narrow first end connected to the deshielder and a narrow second end connected to the other tab thereby forming a frangible point between the tabs, said at least one peg comprising a first part forming an abutment able to cooperate with the first tab during the removal of said deshielder, and a second part able to cooperate with the second tab during the removal of said deshielder.

Preferably, the breaking threshold of the frangible point is lower than the breaking thresholds of the connections between the first ends of the tabs and the deshielder.

According to a feature of the invention, the first and second parts of said peg are spaced one to another perpendicularly to the longitudinal axis of said device, said deshielder comprising a guiding tongue extending between said first and second parts of said peg.

According to another embodiment of the invention, the housing is mounted into a tubular part of the deshielder, said deshielder comprising at least one flexible leg extending inwardly into the tubular part, said leg cooperating with a complementary recess formed on the housing, thereby forming snap-fit means, the free end of the flexible leg forming an abutment for the distal end of the housing after the removal of the deshielder from the housing, thereby preventing the deshielder to be put back on the housing.

According to a still another embodiment of the invention the deshielder comprises a ring and a cap, said ring being mounted on the housing and frangibly connected to the cap.

Preferably, the cap comprises at least one window extending from the proximal edge of the cap, said ring comprising at least one flexible hook extending into said window, said hook being frangibly connected to the cap, for example by welding.

According to a feature of the invention, the ring comprises at least two flexible hooks extending into said window.

Preferably, at least one of said flexible hooks comprises a different thickness or shape relative to the other one, so that the breaking thresholds of the corresponding frangible connections are different.

Alternatively, the housing is equipped with at least one cutting element extending into the window of the cap and able to cut the frangible connection during the removal of the cap.

Preferably, the housing is equipped with a first and a second cutting elements, respectively able to cut the frangible connections of a first and a second hook, the second cutting element being axially spaced with regard to the first cutting element along the longitudinal axis of said device.

According to another embodiment of the invention, at least one deformable arm equipped with a hook is provided on one of the sleeve or housing and for engaging a complementary recess or groove provided on the other of the sleeve or housing, in a mounted state of the deshielder, thereby forming press-fit means.

According to a feature of the invention, after the removal of said at least one part of said deshielder, said hook forms an abutment that prevents the deshielder to be put back on the housing.

Preferably, the cap comprises flexible wings extending substantially perpendicular to the longitudinal axis of the deshielder, the flexible wings comprising free ends spaced one to another thereby defining an opening, the sleeve comprising, at its distal end, a grooved pin engaged into said opening.

According to a still another embodiment of the invention, the housing comprises at least one abutment, a first part of the ring resting on said abutment during removal of the cap, said ring being deformable so that a second part of the ring is movable along the housing during removal of said cap.

Preferably, the housing comprises at least a first and a second abutments axially spaced along the longitudinal axis of said device, the first and the second abutments being respectively able to cooperate with the first and the second parts of the ring.

Alternatively, said first abutment is formed by a first peg, said second abutment is formed by a second peg, each peg extending along the longitudinal axis of said device, the first and the second pegs having two different lengths.

The device of the invention will now be further described in reference to the following description and attached drawings in which:

FIG. 3 is a partial front view of a first embodiment of the invention;

FIG. 4 is a partial side view of the embodiment of FIG. 3;

FIG. 5 is a partial longitudinal cross view of the embodiment of FIGS. 3 and 4, according to the line V-V of FIG. 4;

FIGS. 23 to 25 are views corresponding to FIGS. 20 to 22, showing a ninth embodiment of the invention.

Figure 1:
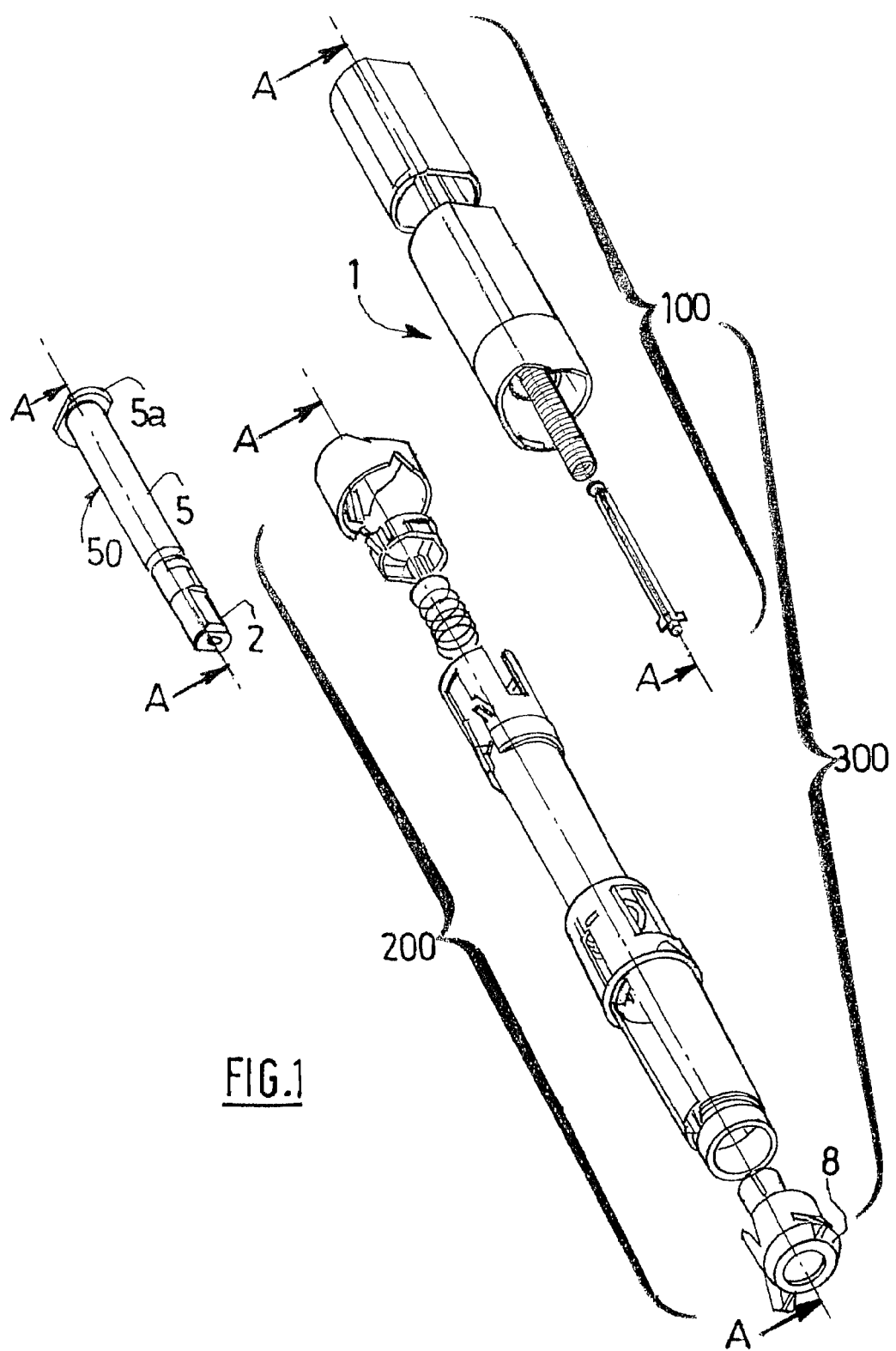
FIG. 1 is an exploded perspective view of an embodiment of the device of the invention.

Referring now to the drawings, the present invention will now be described in detail. FIG. 1 shows an exploded perspective view of a device for automatic injection according to an embodiment of the present invention and generally designated by reference number 1. The inventive device 1 comprises a housing 300 comprised of an upper housing assembly 100 and a lower housing assembly 200 that may be connected to each other by means of a snap-fit connection, screw-type connection, bayonet connection, or other means of connecting two parts together, in an unreleasable way or not. When the device of the injection is of a single use type, the means for connecting the upper housing assembly 100 to the lower housing assembly 200 are made unreachable to the user. A container 50 such as, for example, a syringe, is received in at least one of the upper and lower housing assemblies 100, 200. Preferably, the container 50 is partially received in each of the upper and lower housing assemblies 100, 200, as discussed in more detail herein. The container 50 has a flange 5a defined at an open proximal end, and an injection needle 6 (see, e.g., FIG. 2) at a substantially closed distal end 5b. Lateral walls 5 extend between the proximal and distal ends and define a reservoir 5c sized and shaped to contain a predetermined amount of a product 3 for injection. The injection needle 6 may be fixed to the distal end 5b, or removable therefrom, as a matter of design choice. The injection needle 6 is in fluid communication with the reservoir 5c and provides an outlet port of the container 50 for the product 3. A needle shield 2 is provided at the distal end of the container 50 to cover and protect the needle 6 before use of the device 1. The needle shield 2 also provides for a sealing means of the distal end of the container 50 before use. A piston 7 is provided in the container 50 and which is movable within the reservoir 5c. Movement of the piston 7 causes the product 3 to be expelled from said container 50 through the injection needle 6 during the injection of the product 3 into the patient.

Figure 2:
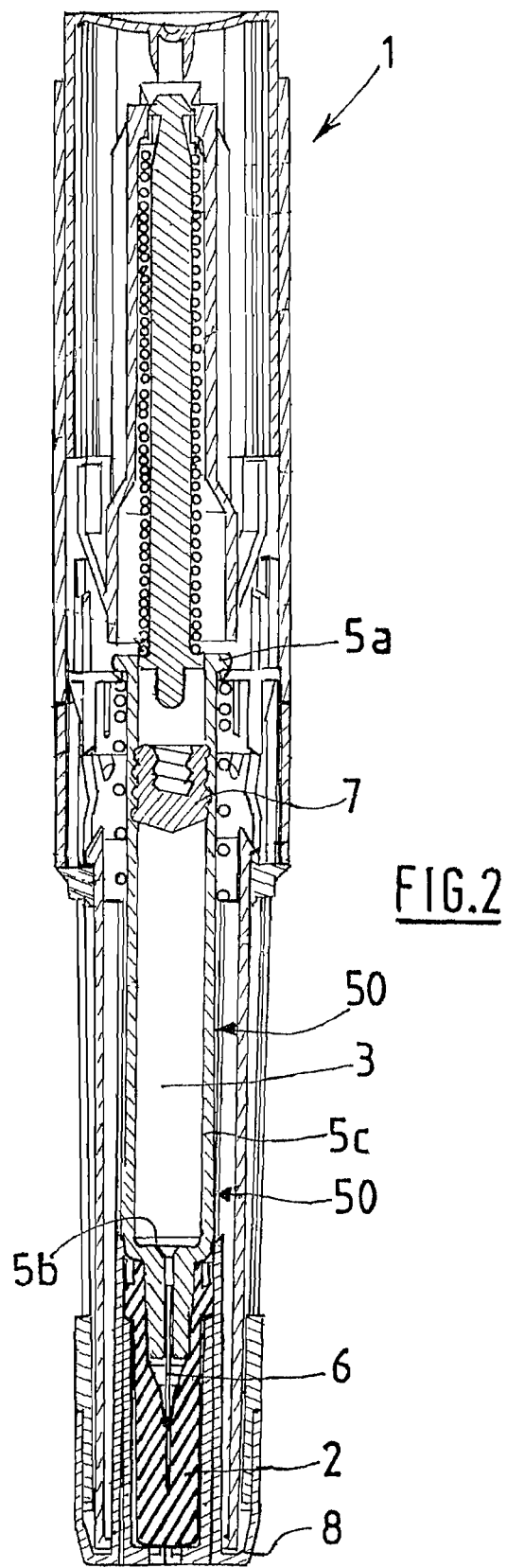
FIG. 2 is a longitudinal cross section view of the device of FIG. 1, before use, with a neddle shield and a deshielder.

The device 1 of the present invention is also provided with a deshielder 8 for removing the needle shield 2. As shown in FIGS. 1 and 2, the deshielder 8 comprises a tubular part carrying the needle shield 2. The deshielder 8 is coupled to the needle shield 2. Prior to use of the device 1, a user removes the deshielder 8, which also removes the needle shield 2.

The deshielder 8 is being mounted on the housing 300 in a separable manner, for example through breakable or snap-fit means, said deshielder 8 comprising tamper evidence means that are activated by the removal of at least one part of said deshielder 8, the at least one part of said deshielder being able to be removed from the housing by exerting a force equal or below 30 N (Newtons), preferably ranging from 2 to 30 N.

The invention concerns in particular the tamper evidence means and the separable connection between the deshielder and the body.

A first embodiment of the invention is illustrated in FIGS. 3 to 5.

As it can be seen, the tamper evidence means of the deshielder comprise two opposite legs 10 located on the housing 300. Each leg 10 comprises a first part 11 extending outwardly from the deshielder and a second part 12 extending longitudinally and equipped with a hook 13 extending into the deshielder 8. Each leg 10 is disposed in a lateral opening and is linked to the deshielder 8 by means of lateral bridges 14 enabling the leg 10 to be pivoted or swivelled with regard to the deshielder 8 when actuated by the user.

Each hook 13 cooperates with a complementary recess 15 arranged in the housing 300. When the legs 10 are actuated, the hooks 13 are disengaged from the recess 15 and the deshielder 8 can be removed. On the contrary, when the legs 10 are not actuated, the hooks 13 secure the deshielder 8 in position with regard to the housing 300.

In addition a window 16 is located on the deshielder 8, said window 16 extending from the proximal end of the deshielder 8. A frangible tongue 17 extends into the window 16, in a direction substantially perpendicular to the longitudinal axis A of said device. A peg 18 extends from the housing 300, said peg 18 being engaged into the window 16 when the deshielder 8 is in its non removed state, said peg 18 being designed to break said frangible tongue 17 when said deshielder 8 is removed from the housing 300.

The frangible tongue 17 and the peg 18 are thereby forming the tamper evidence means.

The traction force exerted by the user to remove the deshielder 8 can be considerably reduced, and is effective below or equal to 30 Newtons, because the legs 10 hold in place the deshielder 8 on the housing 300 before removal. Therefore, the tamper evidence means do not have to provide such function and the strength of the frangible tongue 17 can be reduced.

A second embodiment of the invention is shown on FIGS. 6 to 11.

In this embodiment, the components having a function similar to those detailed above are designated by the same reference.

The tamper evidence means comprise two pegs 18 located on the housing 300 and extending opposite one to another from the housing 300, two windows 16 located on the deshielder 8 and a frangible tongue 17 extending into each window 16, in a direction substantially perpendicular to the longitudinal axis A of said device.

Each peg 18 is engaged into the corresponding window 16 before activation of the tamper evidence means, said peg 18 being designed to break said frangible tongue 17 when the deshielder 18 is removed from the housing 300.

Figure 6:
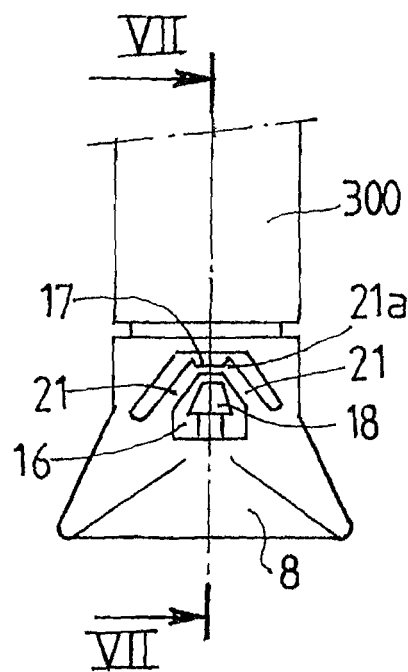
FIG. 6 is a front view of a second embodiment of the invention, in a mounted state of the deshielder.
Figure 7:
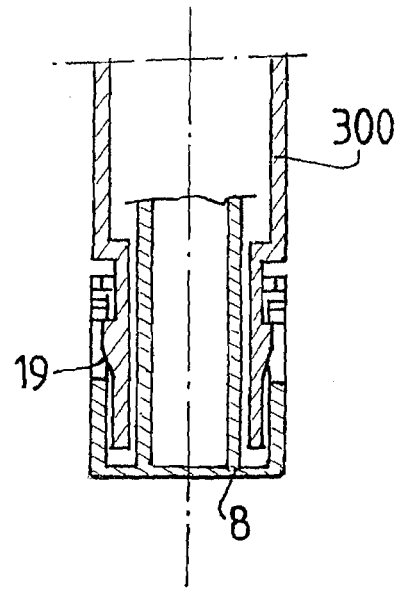
FIG. 7 is a partial cut view according to the line VII-VII of FIG. 6.
Figure 11:
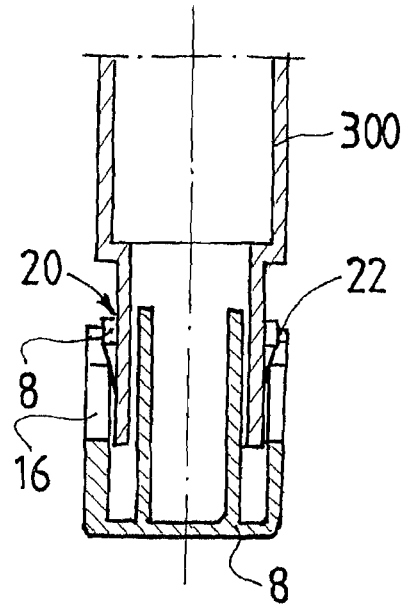

More particularly, each peg 18 has a trapezoidal shape, as detailed on FIG. 6, the peg 18 defining a slope 19 inwardly in direction of the distal end, the proximal end of the peg defining an abutment 20 (see FIGS. 7 and 11).

The deshielder 8 receives the distal end of the housing 300.

In addition, each window 16 of the deshielder 8 comprises two leg 21 extending into it, in the proximal direction, the free ends of the leg 21 being linked by the frangible tongue 17 in the non removed state of the deshielder.

The peg 18 and the leg 21 are designed in such a manner that the abutment 20 is able to cooperate with the frangible tongue 17 during removal of the deshielder 8 so that the frangible tongue 17 is removed from at least one leg 21.

In addition, the proximal edge 22 of the deshielder 8 comprises recesses enabling the movement of the pegs 8 without coming in abutment with said edge 22 (see FIG. 11).

Figure 8:
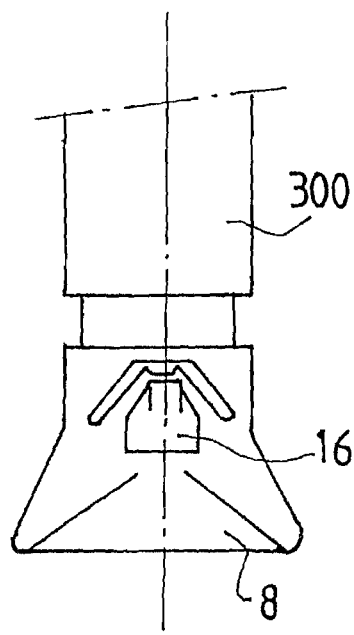
FIGS. 8 and 9 are views corresponding to FIGS. 6 and 7, showing the mounting of the deshielder on the housing.
Figure 9:
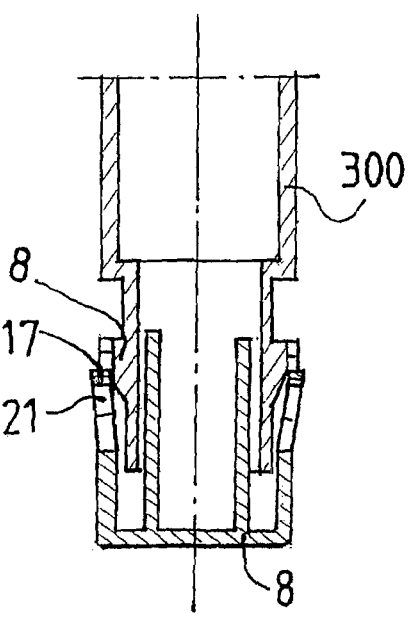

As it can be seen on FIGS. 8 and 9, when positioning for the first time the deshielder 8 on the housing 300, the slope 19 of the peg 18 pushes the flexible leg 21 and the peg 18 is inserted in the aperture delimited by the leg 21 and the frangible tongue 17.

Figure 10:
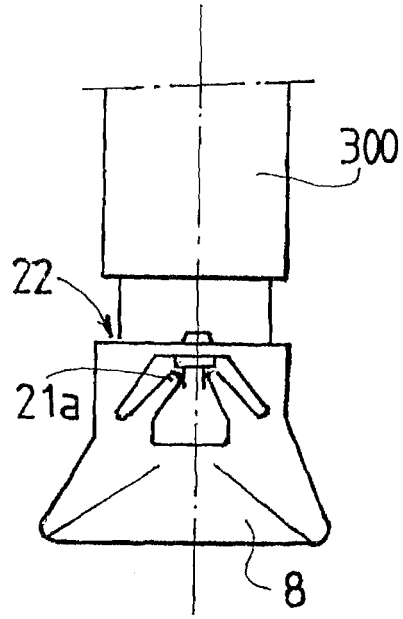
FIGS. 10 and 11 are views corresponding to FIGS. 6 and 7, illustrating the removal of the deshielder with regard to the housing.

As it can be seen on FIGS. 10 and 11, the abutment 20 cooperates with the frangible tongue 17 during the removal of the deshielder so that said frangible tongue 17 is separated from at least one of the leg 21. After complete removal of the deshielder 8, the free ends 21a of the legs 21 come closer one to another due to the elasticity of the legs 21, thereby defining a stop on which the peg 18 comes in abutment if the user intends to recap the deshielder 8.

Consequently the legs 21 prevent the deshielder 8 to be put back on the housing 300.

Figure 12:
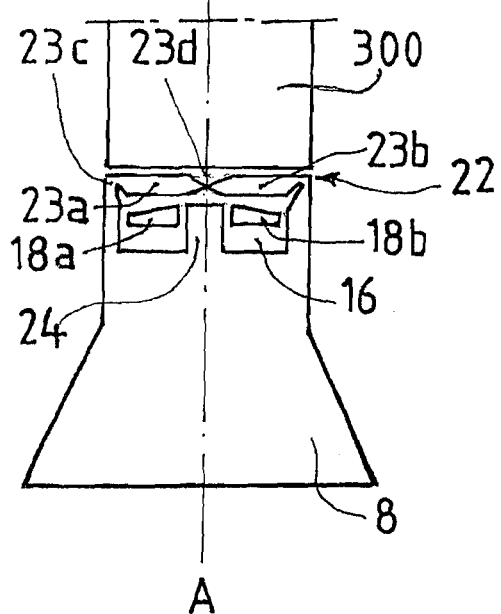
FIGS. 12 and 13 are partial front views of a third embodiment of the invention, respectively in a mounted and removed position of the deshielder.
Figure 13:
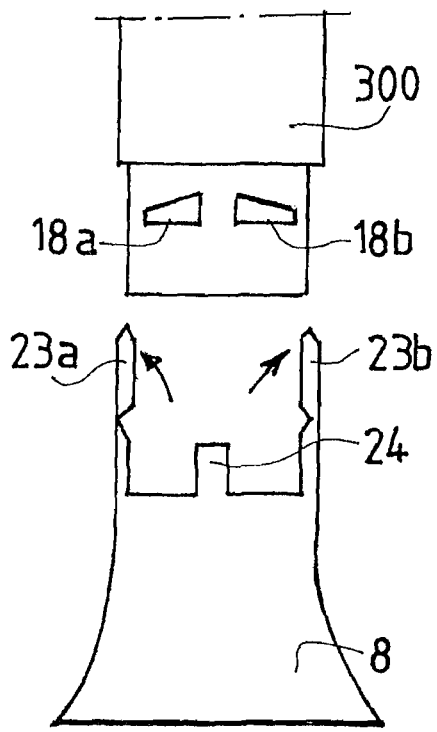

A third embodiment of the invention is depicted on FIGS. 12 and 13.

In this embodiment, the window 16 extends from the proximal edge 22 of the deshielder 8. The deshielder comprises a frangible tongue having a first and second tabs 23a, 23b, each tab comprising a narrow first end 23c connected to the deshielder 8 and a narrow second end 23d connected to the other tab thereby forming a frangible point between the tabs 23, 24.

The breaking threshold of the frangible point is lower than the breaking thresholds of the connections between the first ends of the tabs 23, 24 and the deshielder 8.

In addition, the peg 18 comprises a first part 18a forming an abutment able to cooperate with the first tab 23a during the removal of said deshielder 8, and a second part 18b able to cooperate with the second tab 23b during the removal of said deshielder 8. The first and second parts 18a, 18b of said peg 18 are spaced one to another perpendicularly to the longitudinal axis A of said device, said deshielder 8 comprising a guiding tongue 24 extending between said first and second parts 18a, 18b of said peg.

Therefore, during removal of the deshielder 8, the peg 18 break the frangible point of the frangible tongue 17 and the first and the second tabs 18a, 18b are moved aside one to another. In addition, each tab 18a, 18b remains connected to the deshielder 8 through said narrow first end 23c forming a pivot for the corresponding tab with regard to the deshielder 8.

Figure 14:
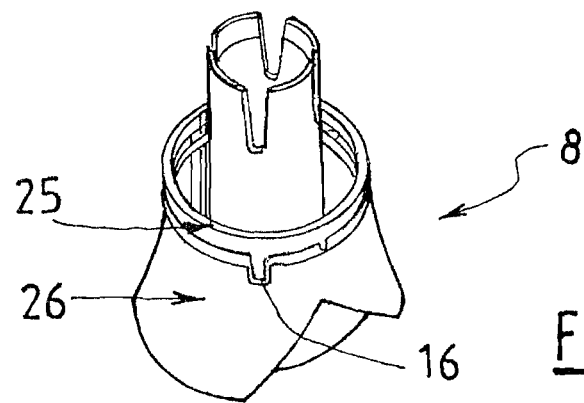
FIG. 14 is a perspective view of the deshielder of a fourth embodiment of the invention.
Figure 15:
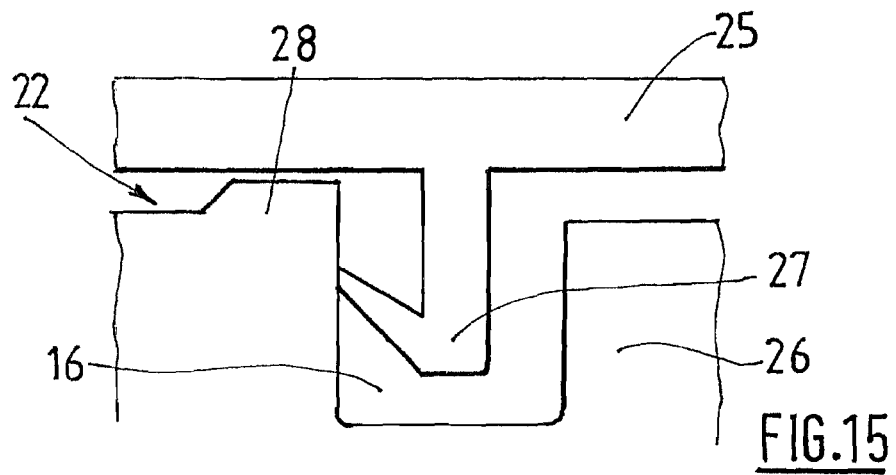
FIG. 15 is an enlarged view of the connection between the cap and the ring of the deshielder of FIG. 14.
Figure 16:
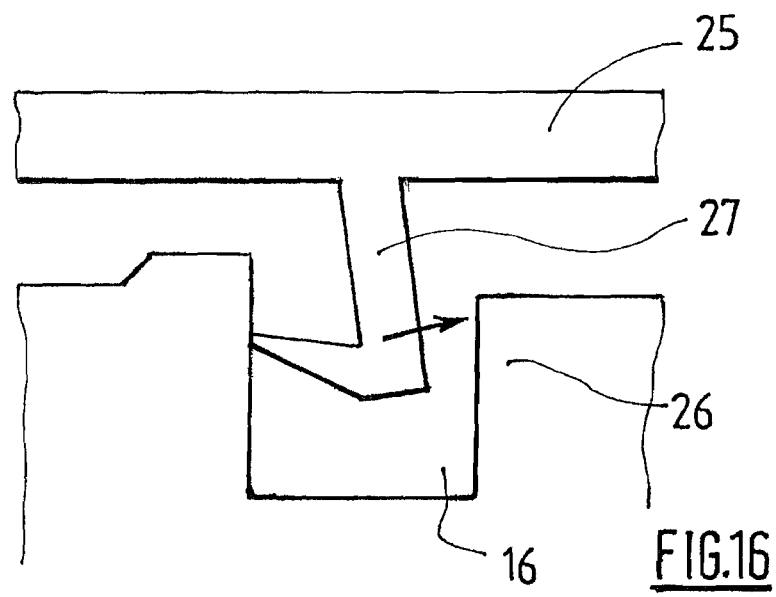
FIG. 16 is a view corresponding to FIG. 15 during removal of the deshielder.

A fourth embodiment of the invention is illustrated on FIGS. 14 to 16.

In this embodiment, the deshielder 8 comprises a ring 25 and a cap 26, said ring 25 being mounted on the housing 300 and frangibly connected to the cap 26.

The cap 26 comprises a plurality of windows 16 extending from the proximal edge 22 of the cap 26, said ring 25 comprising a plurality of flexible hooks 27 extending into the corresponding windows 16, each hook 27 being frangibly connected to the cap 26 by welding.

The cap 26 also comprises an abutment 28 extending from its proximal edge 22 in direction of the ring 25. This abutment 28 prevents from separating the hook 27 from the deshielder 8 while pressing on the deshielder 8. Indeed, the abutment 27 avoids any substantial displacement between the ring 25 and the cap 26 if a user accidentally press on the cap 26.

As it can be seen on FIG. 16, the flexible hook 27 firstly tends to bend during removal the cap 26 and, when the traction force exerted by the user is sufficient, the hook 27 is separated from the cap 26.

Figure 17:
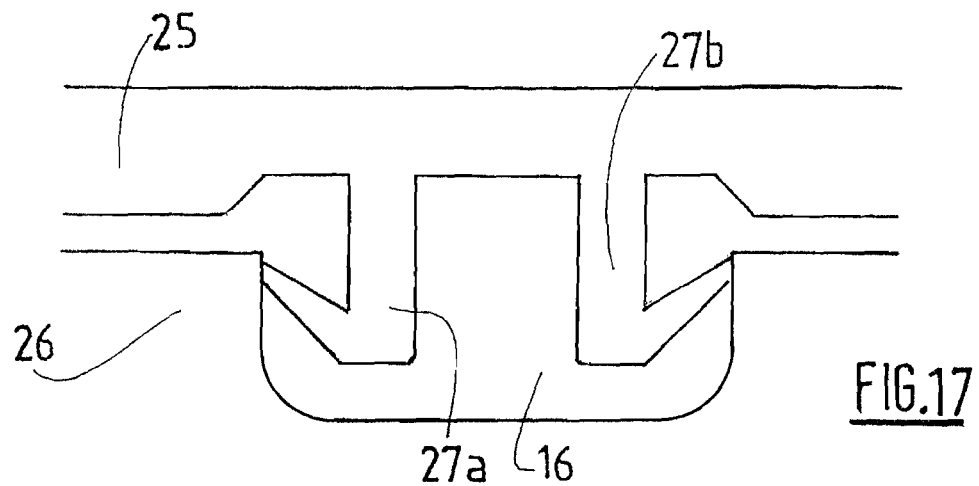
FIG. 17 is a view corresponding to FIG. 15 of a fifth embodiment of the invention.

In another embodiment of the invention depicted on FIG. 17, the ring 25 comprises two flexible hooks 27a, 27b extending into said window 16 and arranged in the opposite direction one to another.

Figure 18:
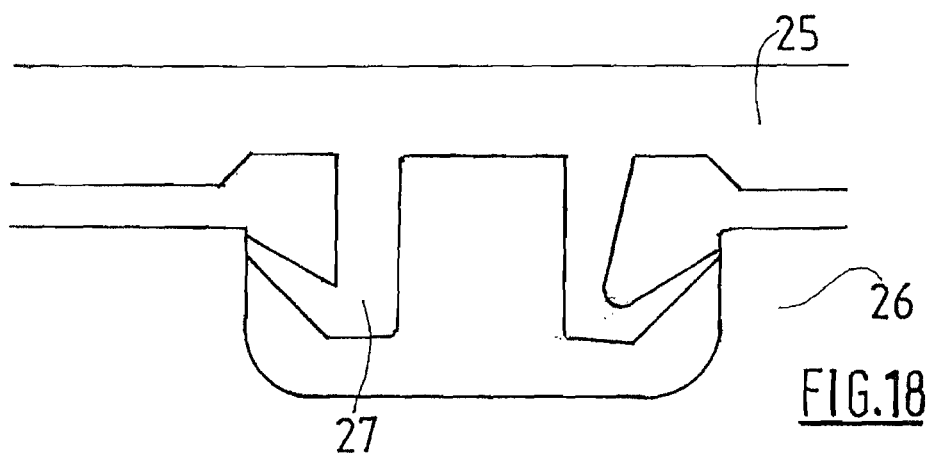
FIG. 18 is a view corresponding to FIG. 14 of a sixth embodiment of the invention.

In a still another embodiment shown on FIG. 18, each hook 27a, 27b comprises a different thickness or shape relative to the other one, so that the breaking thresholds of the corresponding frangible connections with the cap 26 are different.

Therefore, during removal of the deshielder by the user, the hook 27b, which is thinner than the hook 27a, will break in a first time and the hook 27a will break in a second time.

The traction force needed for removing the cap 26 can therefore be reduced because only one hook 27a, 27b needs to be broken at once. Such force is effective for removing the cap 26 at a value equal or less than 30 Newtons.

Figure 19:
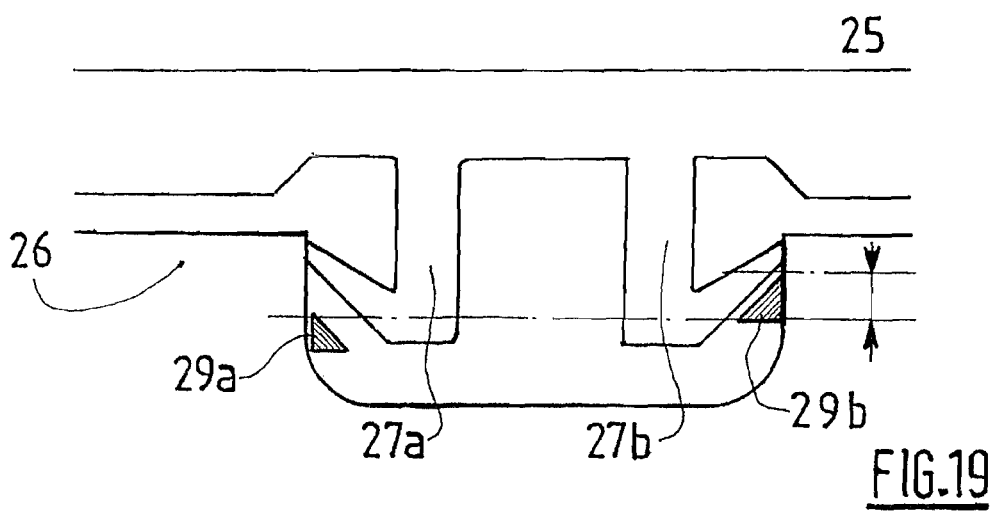
FIG. 19 is a view corresponding to FIG. 18 of a seventh embodiment of the invention.

In a still another embodiment depicted on FIG. 19, the housing 300 is equipped with cutting elements 29a, 29b, respectively able to cut the frangible connections of hooks 27a, 27b. The cutting element 29b is axially spaced with regard to the cutting element 29a in direction of the distal end.

Therefore, during removal of the cap 26, the cutting element 29b first breaks the connection point between the hook 27b and the cap 26. Then, the cutting element 27a breaks the connection point between the hook 27a and the cap 26.

This embodiment provides the advantage exposed above because only one hook 27a, 27b needs to be broken at once.

Figure 22:
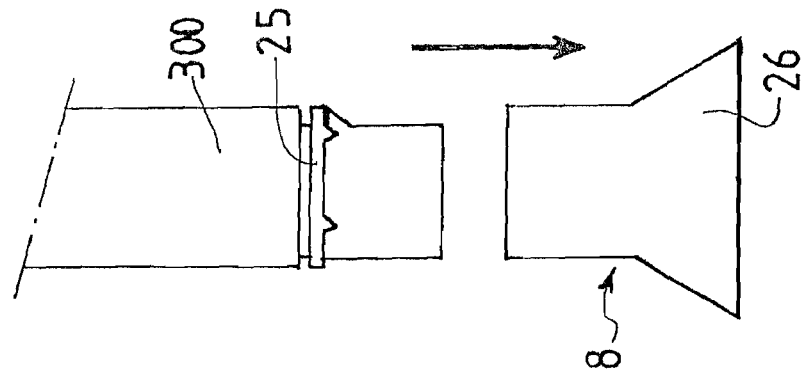
FIG. 22 is a view corresponding to FIG. 20, the deshielder being completely removed from the housing.
Figure 21:
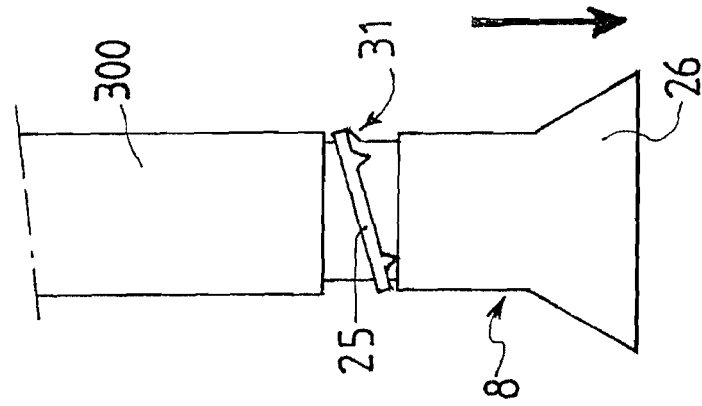
FIG. 21 is a view corresponding to FIG. 20 during the removal of the deshielder.
Figure 20:
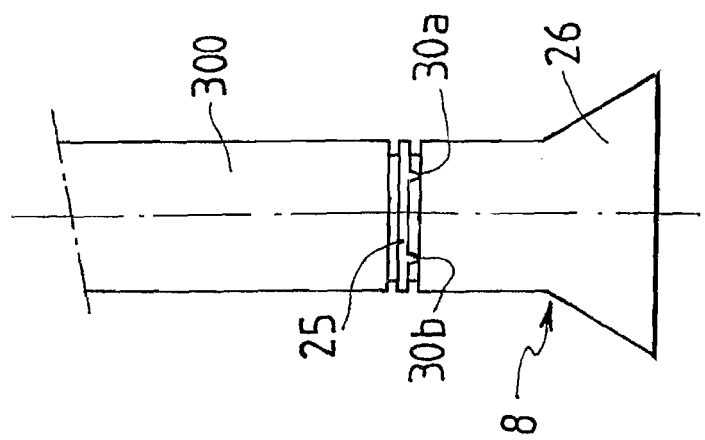
FIG. 20 is a partial front view of an eighth embodiment of the invention.

Another embodiment is illustrated on FIGS. 20 to 22.

In this embodiment the deshielder 8 also comprises a ring 25 and a cap 26 mounted on the housing 300. The ring 25 is connected to the cap 26 through at least a first and a second connection points 30a, 30b spaced one to another perpendicularly to the longitudinal axis A of the housing 300. More specifically, the housing 300 and the deshielder 8 are substantially symmetrical with regard to their longitudinal axis, defining a first and a second parts separated by the plane of symmetry.

The first part of housing 300 is equipped with an abutment 31 (see FIG. 21) extending from the external face of the housing 300 and able to cooperate with the first part of the ring 25.

During removal of the cap 26, the first part of the ring 25 rests on said abutment 31 so as to break the first connection point 30a, said ring 25 being deformable so that the second part of the ring 25 is movable along the housing 300 (FIG. 21).

Then, the second connection point 30b is also broken so that the cap 26 can be completely removed from the housing (FIG. 22).

Again, the traction force needed for removing the cap can therefore be reduced, and can be effective at 30 Newtons or less, because only one frangible connection point needs to be broken at once.

A still another embodiment is depicted on FIGS. 23 to 25. In this embodiment, the housing 300 and the deshielder 8 comprise a first and a second parts 43, 44 separated by the plane of symmetry. The housing 300 has respectively a first and a second pegs 31a, 31b of two different lengths forming a first and a second abutments arranged respectively on the first and the second parts 43, 44.

The proximal end of the first peg 31a is axially spaced from the proximal end of the second pegs 31b in direction of the distal end of the device.

The first and the second pegs 31a, 31b are respectively able to cooperate with the first and the second parts of the ring 25, the ring 25 being linked to the cap 26 by a first and a second legs 32a, 32b arranged respectively on the first and the second parts 43, 44 of the deshielder 8. The first and the second connection points 30a, 30b are formed by narrower portions arranged on the median part of the legs 32a, 32b.

During removal of the cap 26, the first peg 31a abuts on the first part of the ring 25, thereby breaking the first connection point 30a. Therefore, the ring 25 which is still linked to the cap 26 through the second leg 32b is progressively deformed (FIG. 24). Then, the second peg 31b abuts on the second part of the ring 25, thereby breaking the second connection point 30b (FIG. 25). Consequently, the ring 25 is completely separated from the cap 26, said cap 26 being able to be completely removed from the housing 300.

Figure 26:
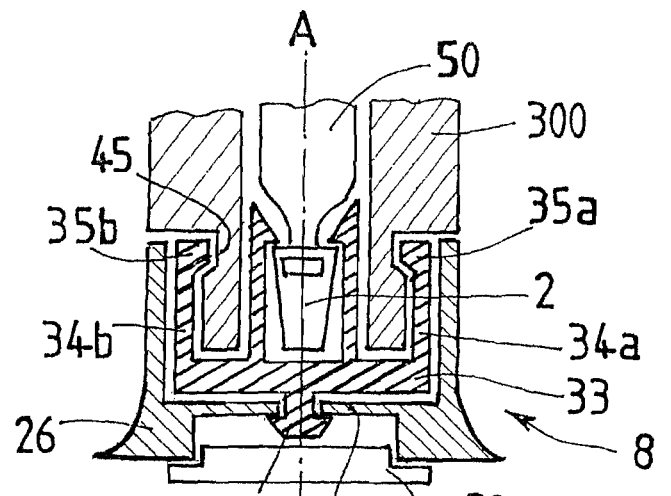
FIG. 26 is a partial longitudinal cross view of a tenth embodiment of the invention.
Figure 27:
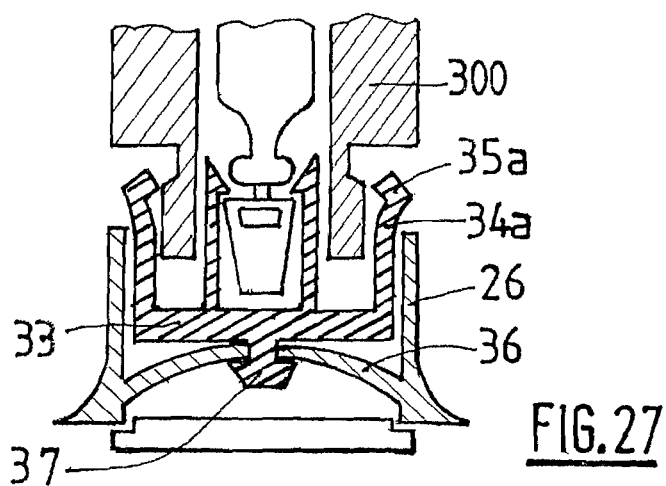
FIG. 27 is a view corresponding to FIG. 26 during removal of the deshielder.
Figure 28:
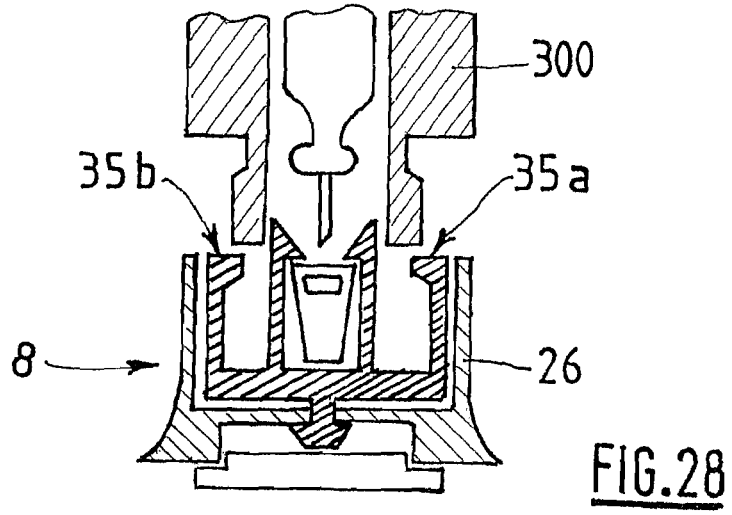
FIG. 28 is a view corresponding to FIG. 26, the deshielder being completely removed from the housing.
Figure 29:
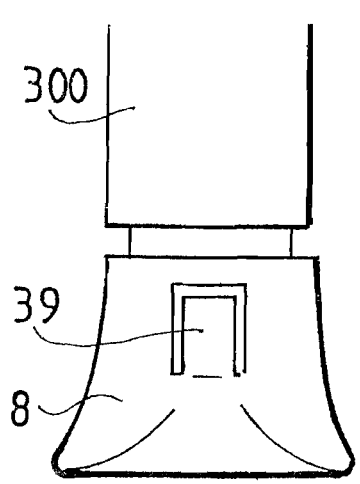
FIGS. 29 and 30 are partial front views of a eleventh embodiment of the invention, respectively in a mounted and removed positions of the deshielder.
Figure 30:
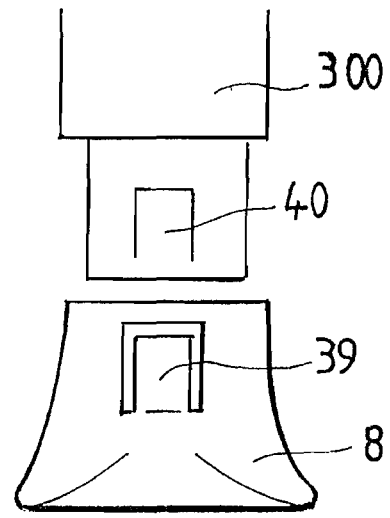
Figure 31:
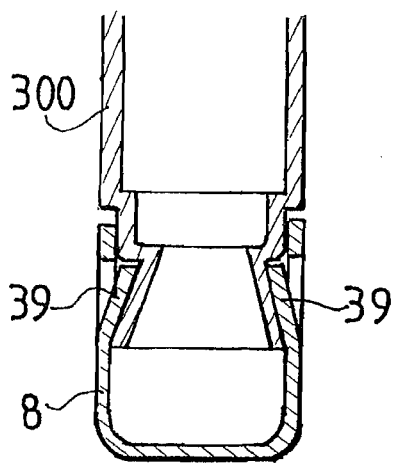
FIGS. 31 and 32 are longitudinal cross views of the device of FIGS. 29 and 30.
Figure 32:
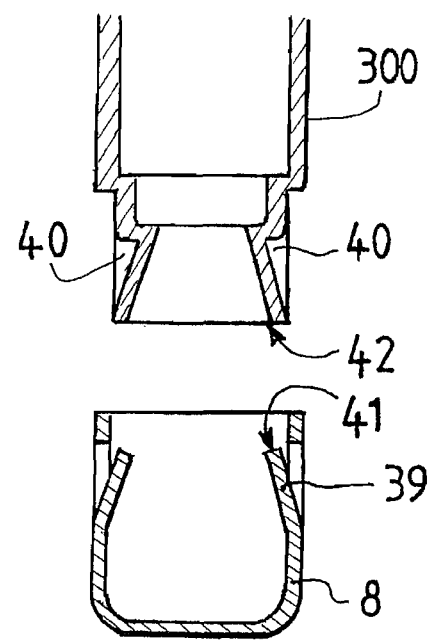

A still another embodiment is shown on FIGS. 26 to 28.

As it can be seen on these Figures, the deshielder 8 comprises a sleeve 33 having two deformable arms 34a, 34b equipped with a hook 35a, 35b engaging a complementary recess or groove 45 arranged on the housing 300 in a mounted state of the deshielder 8, thereby forming press-fit means.

The sleeve 33 is inserted, at least partly, into a tubular cap 26, the sleeve 33 being movable along the longitudinal axis A of the deshielder 8 into the cap 26 between an inserted position (FIG. 26) in which said deformable arms 34a, 34b are inserted into the sleeve 33 so that they cannot be deformed and a pulled out position (FIG. 27) in which the arms 34a, 34b are pulled out of the sleeve 33 and can be deformed.

In addition, the cap 26 comprises flexible wings 36 extending substantially perpendicular, to the longitudinal axis A of the deshielder 8, the flexible wings 36 comprising free ends spaced one to another thereby defining an opening, the sleeve 33 comprising, at its distal end, a grooved pin 37 engaged into said opening.

The distal end of the cap 26 is equipped with a top 38 protecting the grooved pin 37 and the wings 36.

Therefore, as it can be seen on FIG. 27, during removal of the deshielder 8, the flexible wings 36 are progressively deformed so that the sleeve 33 is pulled out of the cap 26. In this position, the arms 34a, 34b can be deformed in order to disengage the deshielder 8 from the housing 300.

After the removal of the deshielder 8, the sleeve 33 is inserted into the cap 26 under the effect of the flexible wings 36 and said hooks 35a, 35b form abutments with respect to the distal end of the housing 300, thereby preventing the deshielder 8 to be put back on the housing 300, as it can be seen on FIG. 28.

Another embodiment of the invention is shown on FIGS. 29 to 32.

In this embodiment, the deshielder 8 comprises two opposite flexible legs 39 extending inwardly into the deshielder 8, each leg 39 cooperating with a complementary recess 40 formed in the housing 300, thereby forming snap-fit means. As it can be seen on FIG. 32, the free ends 41 of the flexible legs 39 form abutments for the distal end 42 of the housing 300 after the removal of the deshielder 8 from the housing 300, thereby preventing the deshielder 8 to be put back on the housing 300.

The invention claimed is:

1. Device for automatic injection of a product into an injection site, said device comprising:
   a housing capable of receiving a container;
   a needle shield for protection of a needle provided on the container prior to use of said device; and
   a deshielder for removing said needle shield from said device, said deshielder being coupled to said needle shield and being mounted on the housing with a separable connection, said deshielder comprising tamper evidence means that are activated by the removal of at least one part of said deshielder, wherein, said at least one part of said deshielder can be removed from the housing by exerting a force equal or below 30 N.

2. Device according to claim 1, wherein said force ranges from 2 to 30 N.

3. Device according to claim 1, wherein said tamper evidence means comprise at least one peg located on the housing, at least one window located on the deshielder and at least one frangible tongue extending into the window, in a direction substantially perpendicular to the longitudinal axis of said device, said peg being engaged into the window before activation of the tamper evidence means, said peg being designed to break said frangible tongue when said part of the deshielder is removed from the housing.

4. Device according to claim 3, wherein said window extends from the proximal end of the deshielder.

5. Device according to claim 4, wherein the deshielder comprises at least one leg articulated on the deshielder and extending along the longitudinal axis of said deshielder, said leg comprising an end forming a hook that cooperate with at least one complementary recess formed in the housing, so as to couple said deshielder to said housing.

6. Device according to claim 3, wherein the deshielder comprises a tubular part receiving a part of the housing, said window being formed on said tubular part, said deshielder comprising at least two legs extending into the window, in the proximal direction, the free ends of the legs being linked by a frangible tongue.

7. Device according to claim 6, wherein, in the removed state of the deshielder, the frangible tongue is separated from at least one of the legs, the free ends of said legs then defining a stop on which the peg comes in abutment, thereby preventing the deshielder to be put back on the housing.

8. Device according to claim 3, wherein said at least one frangible tongue comprises a first and second tabs, each tab comprising a narrow first end connected to the deshielder and a narrow second end connected to the other tab thereby forming a frangible point between the tabs, said at least one peg comprising a first part forming an abutment able to cooperate with the first tab during the removal of said deshielder, and a second part able to cooperate with the second tab during the removal of said deshielder.

9. Device according to claim 8, wherein the breaking threshold of the frangible point is lower than the breaking thresholds of the connections between the first ends of the tabs and the deshielder.

10. Device according to claim 8, wherein the first and second parts of said peg are spaced one to another perpendicularly to the longitudinal axis of said device, said deshielder comprising a guiding tongue extending between said first and second parts of said peg.

11. Device according to claim 1, wherein the housing is mounted into a tubular part of the deshielder, said deshielder comprising at least one flexible leg extending inwardly into the tubular part, said leg cooperating with a complementary recess formed on the housing, thereby forming snap-fit means, the free end of the flexible leg forming an abutment for the distal end of the housing after the removal of the deshielder from the housing, thereby preventing the deshielder to be put back on the housing.

12. Device according to claim 1, wherein the deshielder comprises a ring and a cap, said ring being mounted on the housing and frangibly connected to the cap.

13. Device according to claim 12, wherein the cap comprises at least one window extending from the proximal edge of the cap, said ring comprising at least one flexible hook extending into said window, said hook being frangibly connected to the cap.

14. Device according to claim 13, wherein the ring comprises at least two flexible hooks extending into said window.

15. Device according to claim 14, wherein at least one of said flexible hooks comprises a different thickness or shape relative to the other one, so that the breaking thresholds of the corresponding frangible connections are different.

16. Device according to claim 13, wherein the housing is equipped with at least one cutting element extending into the window of the cap and able to cut the frangible connection during the removal of the cap.

17. Device according to claim 16, wherein the housing is equipped with a first and a second cutting elements, respectively able to cut the frangible connections of a first and a second hook, the second cutting element being axially spaced with regard to the first cutting element along the longitudinal axis of said device.

18. Device according to claim 1, wherein at least one deformable arm equipped with a hook is provided on one of a sleeve or the housing and for engaging a complementary recess or groove provided on the other of the sleeve or housing, in a mounted state of the deshielder, thereby forming press-fit means.

19. Device according to claim 18, wherein, after the removal of said at least one part of said deshielder said hook forms an abutment that prevents the deshielder to be put back on the housing.

20. Device according to claim 18, wherein the cap comprises flexible wings extending substantially perpendicular to the longitudinal axis of the deshielder, the flexible wings comprising free ends spaced one to another thereby defining an opening, the sleeve comprising, at its distal end, a grooved pin engaged into said opening.

21. Device according to claim 12, wherein the housing comprises at least one abutment, a first part of the ring resting on said abutment during removal of the cap, said ring being deformable so that a second part of the ring is movable along the housing during removal of said cap.

22. Device according to claim 21, wherein the housing comprises at least a first and a second abutments axially spaced along the longitudinal axis of said device, the first and the second abutments being respectively able to cooperate with the first and the second parts of the ring.

23. Device according to claim 22, wherein said first abutment is formed by a first peg, said second abutment is formed by a second peg, each peg extending along the longitudinal axis of said device, the first and the second pegs having two different lengths.

24. Device according to claim 1, wherein said separable connection is breakable.

25. Device according to claim 1, wherein said separable connection includes snap-fit means.

26. Device according to claim 1, wherein said separable connection being separately provided from said tamper evidence means.

27. Device according to claim 13, wherein said hook being frangibly connected to the cap by welding.

* * * * *